US00PP31222P2

(12) United States Plant Patent
Hansen

(10) Patent No.: US PP31,222 P2
(45) Date of Patent: Dec. 10, 2019

(54) ***HEUCHERA* PLANT NAMED 'WILDBERRY'**

(50) Latin Name: ***Heuchera* hybrid**
Varietal Denomination: Wildberry

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 16/350,491

(22) Filed: Nov. 21, 2018

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./263.1, 440
See application file for complete search history.

*Primary Examiner* — Susan McCormick Ewoldt
*Assistant Examiner* — Karen M Redden

(57) ABSTRACT

The new and distinct hybrid of *Heuchera* plant named 'Wildberry' with many large, rounded-palmate, shallowly dissected foliage and large, dense, mounded habit. The leaf blades are deep to strong purplish-red with darker greyed purple surrounding veins. Branched panicles produce complimentary strong purplish-red calyces and flower effect for about five weeks beginning mid-summer. The new plant is vigorous and produces large clumps with many large leaves.

1 Drawing Sheet

Botanical denomination: *Heuchera* hybrid.
Variety denomination: 'Wildberry'.

STATEMENT REGARDING PRIOR DISCLOSURES UNDER 37 CFR 1.77(b)(6)

The first public disclosure of the claimed plant, in the form of a sale, was made by Walters Gardens, Inc. on Jul. 9, 2018. Prior to that, on Nov. 28, 2017 the claimed plant was displayed as a photograph without description in a promotional calendar by Walters Gardens, Inc., who obtained the plant and all information relating thereto, from the inventor. No plants of *Heuchera* 'Wildberry' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of Coral Bells in the Saxifragaceae family and given the cultivar name of 'Wildberry'. *Heuchera* 'Wildberry' was hybridized by the inventor on Sep. 1, 2015 at a wholesale perennial nursery in Zeeland, Mich., USA. The seed or female parent was the proprietary, unreleased, unnamed hybrid known only by the breeder code 13-809-01 (not patented) and the pollen or male parent was 'Black Pearl' U.S. Plant Pat. No. 29,395.

*Heuchera* 'Wildberry' was first selected in the fall of 2016 from among many other seedlings from the same cross and hundreds of other crosses and assigned the breeder code 15-238-6 through the remaining evaluation process. *Heuchera* 'Wildberry' has been asexually propagated by division at the same nursery in Zeeland, Mich. in 2016 and by sterile, shoot-tip, tissue culture propagation, and the resultant plants have remained stable and continued to exhibit the same characteristics as the original plant for multiple generations.

BRIEF SUMMARY OF THE INVENTION

The nearest comparison varieties include: the male parent 'Black Pearl', 'Blackberry Ice' U.S. Plant Pat. No. 27,788, 'Wild Rose' U.S. Plant Pat. No. 29,923, 'TNHEUFP' U.S. Plant Pat. No. 26,358 and 'Grape Expectations' U.S. Plant Pat. No. 26,894. The female parent nor photographs of the female parent were not maintained, so no further comparison with the new plant is possible. 'Black Pearl' has darker greyed-purple foliage that is flatter than the new plant. 'Blackberry Ice' smaller leaves that develop a silver overlay on the leaves but without the glowing purple hue of the new plant and the flowers are creamy white. 'Wild Rose' has a slighter smaller habit and the leaves develop a silver marbling. 'TNHEURP' has smaller, darker purple leaves with less contrast to dark veins, and the lobes are slightly deeper cleft. 'Grape Expectations' has a more upright flowering habit of creamy white flowers and the foliage develops a silver marbling. *Heuchera* 'Wildberry' differs from its parents as well as all other coral bells known to the applicant in the following combined traits:

1. Large, rounded-palmate foliage on dense mounded plant.
2. Leaves are shiny with bold dark purple coloration.
3. Leaf blades are shallowly dissected with apices and lobes rounded and micro-apiculate.
4. Flower effect is deep to strong purplish-red for five weeks in mid-summer.
5. The new plant is vigorous and produces medium dense clumps and many individual leaves.

BRIEF DESCRIPTION OF THE DRAWINGS

The photographs of 'Wildberry' demonstrate the overall appearance of the plant including the unique traits of a container-grown plant in a greenhouse in Zeeland, Mich. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
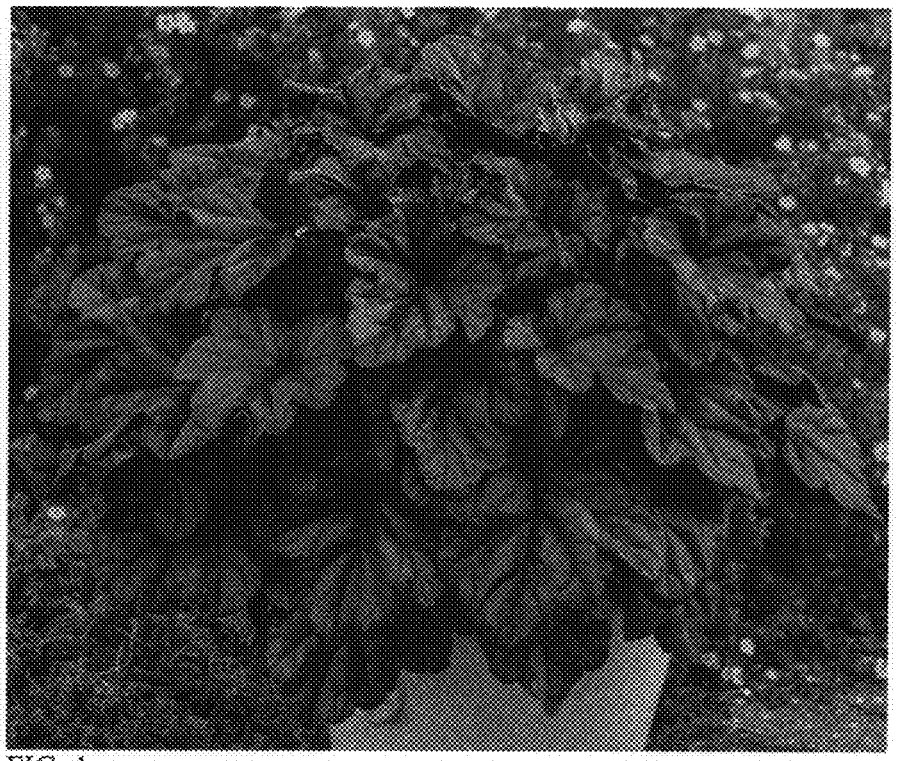
FIG. 1 shows a two-year-old plant prior to flowering.
Figure 2:
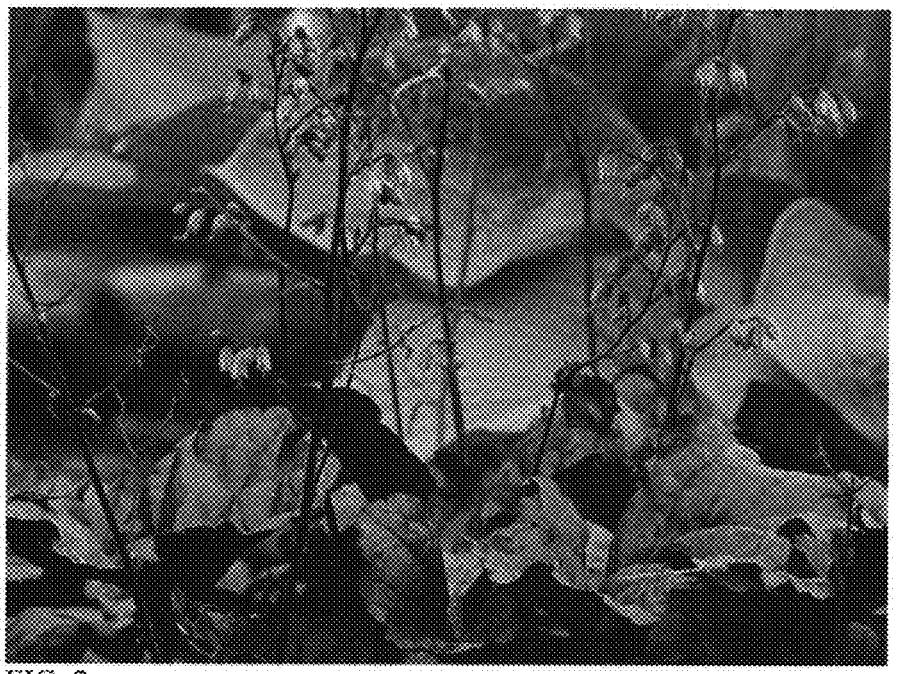
FIG. 2 shows a close-up of a flower panicles with buds and flowers from a two-year-old plant.

The following description is based on a two-year-old plants growing in a partially shaded greenhouse and in a landscape in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was the proprietary, unreleased hybrid known as 13-809-1 comprising crosses with 'Mocha Mint' (not patented), 'Mocha' U.S. Plant Pat. No. 18,386, 'Tiramisu' U.S. Plant Pat. No. 20,429, 'Georgia Plum' U.S. Plant Pat. No. 24,507 and 'Stainless Steel' U.S. Plant Pat. No. 23,349; the male or pollen parent was 'Black Pearl';

Plant habit: Hardy herbaceous perennial with basal rosette of foliage; mounded foliage about 33.0 cm tall and 65.0 cm in diameter with scapes to about 55.0 cm long; with 6 stems per plant to about 22.0 cm long and 2.2 cm diameter at base, up to 48 leaves per stem;

Roots: Fibrous, finely branched;

Growth rate: Rapid, rooting from cutting in two weeks and finishing in three-liter container in about two and a half months;

Foliage: Rounded-palmate; apex and lobe apices rounded and micro-apiculate; base cordate with basal lobes nearly touching to lightly overlapping to about 0.5 cm; margins crenate, ciliolate, mucronulate; glabrous to sparsely micro-puberulent and lustrous adaxial, glabrous to sparsely puberulent and matte abaxial; palmately shallowly lobed with five main lobes dissected less than one-quarter of the way to petiole; held nearly horizontal to slightly drooping toward perimeter of plant; margin nearly flat, not sinuate; slightly folded upwardly along main veins;

Leaf blade size: To about 15.5 cm wide and 16.0 cm long, average about 12.0 cm wide and 12.2 cm long;

Leaf color: Spring and young emerging leaves adaxial nearest RHS N79B with no silver and dark green marbling surrounding the veins, spring and young emerging leaves abaxial nearest RHS 187B; mature mid-season leaves adaxial between RHS N79B and RHS N79C, abaxial mature mid-season leaves nearest RHS N186B; mid-fall color adaxial between RHS N79B and RHS N187B, mid-fall abaxial between RHS N79A and N77A;

Leaf quantity: Dense, about 150 per plant;

Veins: Palmate, slightly puberulent abaxial and glabrous adaxial; costate abaxial, slightly impressed adaxial;

Vein color: Emerging or early spring adaxial nearest RHS 196A with emerging spring abaxial nearest RHS N186D; mid-season and flowering time adaxial nearest RHS N186A, mid-season and flowering time abaxial nearest RHS N186D; fall adaxial nearest RHS N186A, fall abaxial nearest RHS N186D;

Petiole: Cylindrical; base amplexicaul; micro-puberulent; to about 25.5 cm long and 10.0 mm wide base, average about 18.0 cm long and about 8.5 mm diameter base;

Petiole color: Emerging leaf nearest RHS N186D; flowering season mature leaf nearest RHS 187A;

Stipule: Flared at base of petiole; lanceolate; acute apex, base amplexicaul, fused to petiole in basal 10.0 mm; glaucous and glabrous abaxial and adaxial; margin ciliate; to about 18.0 mm long and about 10.0 mm wide at base; with two lateral projections of about 8.0 mm long in distal portion;

Stipule color: Nearest RHS N186D;

Peduncle: Branched panicle; cylindrical; stiff; micro-puberulent; upright; with short branches; to about 55.0 cm long and 4.0 mm diameter at base, average about 52.0 cm tall and 4.0 mm diameter; about 15 per plant with up to about 166 flowers per panicle, average about 150; tightly-branched panicle with up to 14 branches up to 7.0 cm long and 1.0 mm diameter decreasing distally, average 12 branches per panicle; lower branches mostly outwardly; with about three cauline bracts about 3.5 cm apart before flowers and subtending branches; flower density light;

Cauline bracts: Palmate with narrowly dissected lobes; acute apex and lobes; cordate base; to 5.0 cm long and 6.3 cm across, decreasing distally; petiolate; petiole to 3.5 cm long and 3.0 mm wide; micro-puberulent and lustrous adaxial and glabrous and matte abaxial;

Cauline leaf color: Same as basal leaves;

Flowering longevity: Panicle effective for about five weeks; individual flowers about 5 days; self-cleaning;

Peduncle color: Between RHS M186A and RHS 187A;

Pedicel: Cylindrical, puberulent; about 4.0 mm long and 0.7 mm diameter; attitude outwardly to drooping;

Pedicel color: Between RHS N186A and RHS N186B;

Buds one day prior to opening: Ellipsoidal; rounded apex and attenuate base; puberulent to glandular; about 4.0 mm long and 2.5 mm diameter;

Bud color one day prior to opening: Nearest RHS 183B;

Flower: Perfect; campanulate; actinomorphic; about 9.0 mm long to tip of exserted style and 3.5 mm in diameter at corolla face;

Flower attitude: Slightly drooping to drooping;

Calyx: Base fused in proximal 3.0 mm to form hypanthium; puberulent to glandular abaxial, glabrous adaxial; about 5.5 mm long and 3.5 mm wide at apex;

Sepals: Five; lanceolate; acute apex, fused in basal 3.0 mm; to about 5.5 mm long and 1.0 mm wide at fusion;

Sepal color: Abaxial nearest RHS 71B distally and base nearest RHS 71A;

Petals: Five; oblanceolate to spatulate; subacute apex and attenuate base; entire; glabrous abaxial and adaxial; about 2.5 mm long and 1.0 mm wide in middle;

Petal color: Abaxial and adaxial nearest RHS 69D;

Androecium: Five adnate to adaxial sepal about 1.5 mm above base;

*Filaments.*—Five, thin, glabrous; about 2.5 mm long and less than 0.3 mm diameter; color nearest RHS 186D.

*Anthers.*—Ellipsoidal, distinct, basifixed, longitudinal; about 0.7 mm long and about 0.5 mm across; color nearest RHS 17B.

*Pollen.*—Abundant; color nearest RHS 17B.

Gynoecium: One, two-beaked; half-inferior; bifid style with pistil split at ovary; about 9.0 mm long;

*Style.*—Bifid; split apart at apex of ovary; exserted; about 7.5 mm long and about 0.5 mm diameter; color nearest RHS 71D.

*Stigma.*—Acute apex, about 0.1 mm diameter; color nearest RHS 75A.

*Ovary.*—Half-inferior, about 2.0 mm long and 2.0 mm diameter; ellipsoidal to globose, base rounded; color nearest RHS 186C.

Fruit: Small two-beaked capsule; about 2.5 mm long and 2.5 mm across; drying to RHS 200C;

Seeds: Abundant; slightly flattened ellipsoid; about 0.3 mm long, 0.2 mm across and about 0.1 mm thick; color nearest RHS 200A;

Disease and pest tolerance: The new plant grows best with ample moisture and drainage in either part sun or light shade. Cold hardy from USDA zones 4 to 9. Other resistance and tolerance outside of that normal for *Heuchera* is not known.

It is claimed:

1. The new and distinct coral bells plant named *Heuchera* 'Wildberry' as herein described and illustrated.

* * * * *